United States Patent [19]

Krenzer

[11] 4,097,486

[45] * Jun. 27, 1978

[54] HERBICIDAL THIADIAZOLYLIMIDAZOLIDINONE ESTER

[75] Inventor: John Krenzer, Oak Park, Ill.

[73] Assignee: Velsicol Chemical Corporation, Chicago, Ill.

[*] Notice: The portion of the term of this patent subsequent to May 3, 1994, has been disclaimed.

[21] Appl. No.: 736,913

[22] Filed: Oct. 29, 1976

[51] Int. Cl.² ............................................ C07D 285/12
[52] U.S. Cl. .................................. 260/306.8 D; 71/90
[58] Field of Search ...................... 71/90; 260/306.8 D

[56] References Cited

U.S. PATENT DOCUMENTS

| 4,052,191 | 10/1977 | Krenzer | 260/306.8 D |
| 4,052,192 | 10/1977 | Krenzer | 260/306.8 D |
| 4,052,193 | 10/1977 | Krenzer | 260/306.8 D |

Primary Examiner—Richard J. Gallagher
Attorney, Agent, or Firm—Robert J. Schwarz; Dietmar H. Olesch

[57] ABSTRACT

This invention discloses the compound 1-(5-trifluoromethyl-1,3,4-thiadiazol-2-yl)-3,4-dimethyl-5-acetyloxy-1,3-imidazolidin-2-one and its use as a herbicide.

1 Claim, No Drawings

HERBICIDAL THIADIAZOLYLIMIDAZOLIDINONE ESTER

This invention relates to a new composition of matter and more specifically relates to the compound 1-(5-trifluoromethyl-1,3,4-thiadiazol-2-yl)-3,4-dimethyl-5-acetyloxy-1,3-imidazolidin-2-one. The compound of the present invention has the following structural formula:

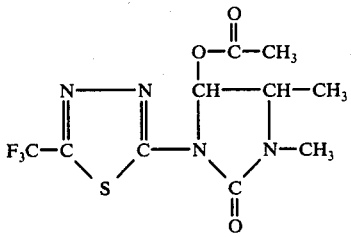

The compound of the present invention has utility as a herbicide.

The manner in which the compound of this invention can be prepared readily is illustrated in the following examples.

EXAMPLE 1

Preparation of 5-Trifluoromethyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-trifluoromethyl-2-amino-1,3,4-thiadiazole (10 grams) in ethyl acetate (300 ml) is added to the reaction vessel, and the resulting mixture is stirred for a period of about 16 hours, resulting in the formation of a precipitate. The reaction mixture is then purged with nitrogen gas to remove unreacted phosgene. The purged mixture is then filtered to recover the desired product 5-trifluoromethyl-1,3,4-thiadiazol-2-yl isocyanate dimer.

EXAMPLE 2

Preparation of the Dimethyl Acetal of 2-[1-Methyl-3-(5-trifluoromethyl-1,3,4-thiadiazol-2-yl)ureido]propionaldehyde A mixture of 5-trifluoromethyl-1,3,4-thiadiazol-2-yl isocyanate dimer (6 grams), the dimethyl acetal of 2-methylaminopropionaldehyde (5.5 grams) and benzene (20 ml) is charged into a glass reaction flask equipped with a mechanical stirrer and thermometer. The reaction mixture is heated on a steam bath with stirring until all reactants have dissolved. After this time the reaction mixture is stripped of benzene to yield the desired product the dimethyl acetal of 2-[1-methyl-3-(5-trifluoromethyl-1,3,4-thiadiazol-2-yl)ureido]propionaldehyde.

EXAMPLE 3

Preparation of 1-(5-Trifluoromethyl-1,3,4-thiadiazol-2-yl)-3,4-dimethyl-5-hydroxy-1,3-imidazolidin-2-one The dimethyl acetal of 2-[1-methyl-3-(5-trifluoromethyl-1,3,4-thiadiazol-2-yl)ureido]propionaldehyde prepared in Example 2, water (150 ml) and concentrated hydrochloric acid (5 ml) are charged into a glass reaction vessel equipped with a mechanical stirrer and thermometer. The reaction mixture is heated on a steam bath for a period of about 30 minutes. After this time ethyl acetate (50 ml) is added to the reaction mixture with stirring and continued heating. The organic phase is then separated from the aqueous phase and is stripped of ethyl acetate to yield the desired product 1-(5-trifluoromethyl-1,3,4-thiadiazol-2-yl)-3,4-dimethyl-5-hydroxy-1,3-imidazolidin-2-one.

EXAMPLE 4

Preparation of 1-(5-Trifluoromethyl-1,3,4-thiadiazol-2-yl)-3,4-dimethyl-5-acetyloxy-1,3-imidazolidin-2-one 1-(5-Trifluoromethyl-1,3,4-thiadiazol-2-yl)-3,4-dimethyl-5-hydroxy-1,3-imidazolidin-2-one (5.0 grams), acetic anhydride (3 ml), methylene chloride (50 ml) and pyridine are charged into a glass reaction vessel with stirring. The reaction mixture is then allowed to stand overnight at room temperature. The reaction mixture is then stripped of solvent under reduced pressure to yield a solid residue. This residue is recrystallized to yield the desired product 1-(5-trifluoromethyl-1,3,4-thiadiazol-2-yl)-3,4-dimethyl-5-acetyloxy-1,3-imidazolidin-2-one.

For practical use as a herbicide the compound of this invention is generally incorporated into herbicidal compositions which comprise an inert carrier and a herbicidally toxic amount of the compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compound is sufficiently soluble in common organic solvents such as kerosene or xylene so that it can be used directly as a solution in these solvents. Frequently, solutions of herbicides can be dispersed under superatmospheric pressure as aerosols. However, preferred liquid herbicidal compositions are emulsifiable concentrates, which comprise the active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 5

Preparation of a Dust

Product of Example 4:10

Powdered Talc:90

The above ingredients are mixed in a mechanical grinder-blender and are ground until a homogeneous, free-flowing dust of the desired particle size is obtained. This dust is suitable for direct application to the site of the weed infestation.

The compound of this invention can be applied as a herbicide in any manner recognized by the art. One method for the control of weeds comprises contacting the locus of said weeds with a herbicidal composition comprising an inert carrier and as an essential active ingredient, in a quantity which is herbicidally toxic to said weeds, the compound of the present invention. The concentration of the new compound of this invention in the herbicidal compositions will vary greatly with the type of formulation and the purpose for which it is designed, but generally the herbicidal compositions will comprise from about 0.05 to about 95 percent by weight of the active compound of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compound of the present invention is also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compound of the present invention provide herbicidal compositions which are more effective in controlling weeds and often provide results unattainable with separate compositions of the individual herbicides. The other herbicides, defoliants, dessicants and plant growth inhibitors, with which the compound of this invention can be used in the herbicidal compositions to control weeds, can include chlorophenoxy herbicides such as 2,4-D, 2,4,5-T, MCPA, MCPB, alachlor, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diluron, linuron, monolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)piperidine, and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like. Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyard grass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflex, yarrow, aster, gromwell, horsetail, ironweed, sesbania, bulrush, cattail, wintercress, horsenettle, nutsedge, milkweed and sicklepod.

Similarly, such weeds can be classified as broadleaf or grassy weeds. It is economically desirable to control the growth of such weeds without damaging beneficial plants or livestock.

The new compound of this invention is particularly valuable for weed control because it is toxic to many species and groups of weeds while it is relatively non-toxic to many beneficial plants. The exact amount of the compound required will depend on a variety of factors, including the hardiness of the particular weed species, weather, type of soil, method of application, the kind of beneficial plants in the same area, and the like. Thus, while the application of up to only about 1 or 2 ounces of the active compound per acre may be sufficient for good control of a light infestation of weeds growing under adverse conditions, the application of 10 pounds or more of active compound per acre may be required for good control of a dense infestation of hardy perennial weeds growing under favorable conditions.

The herbicidal toxicity of the new compound of this invention can be demonstrated by many of the established testing techniques known to the art, such as pre- and post-emergence testing.

The herbicidal activity of the compound of this invention can be demonstrated by experiments carried out for the pre-emergence control of a variety of weeds. In these experiments small plastic greenhouse pots filled with dry soil are seeded with the various weed seeds. Twenty-four hours or less after seeding, the pots are sprayed with water until the soil is wet and the compound 1-(5-trifluoromethyl-1,3,4-thiadiazol-2-yl)-3,4-dimethyl-5-acetyloxy-1,3-imidazolidin-2-one formulated as a solution in an inert solvent is sprayed at the desired concentrations on the surface of the soil.

After spraying, the soil containers are placed in the greenhouse and provided with supplementary heat as required and daily or more frequent watering. The plants are maintained under these conditions for a period of 21 days, at which time the condition of the plants and the degree of injury to the plants is rated on a scale of from 0 to 10, as follows: 0 = no injury, 1,2 = slight injury, 3,4 = moderate injury, 5,6 = moderately severe injury, 7,8,9 = severe injury and 10 = death.

The herbicidal activity of the compound of this invention can also be demonstrated by experiments carried out for the post-emergence control of a variety of weeds. In these experiments the compound of this invention is formulated as a solution in an inert solvent and sprayed at the desired dosage on the foliage of the weeds that have attained a prescribed size. After spraying, the plants are placed in a greenhouse and watered daily or more frequently. Water is not applied to the foliage of the treated plants. The severity of the injury is determined 14 days after treatment and rated on the scale of from 0 to 10 heretofore described.

I claim:
1. The compound 1-(5-trifluoromethyl-1,3,4-thiadiazol-2-yl)-3,4-dimethyl-5-acetyloxy-1,3-imidazolin-2-one.

UNITED STATES PATENT OFFICE
CERTIFICATE OF CORRECTION

PATENT NO. : 4,097,486
DATED : Jun. 27, 1978
INVENTOR(S) : John Krenzer

It is certified that error appears in the above—identified patent and that said Letters Patent are hereby corrected as shown below:

Column 6, line 20 should read -- lidin-2-one --

Signed and Sealed this

Fifth Day of December 1978

[SEAL]

Attest:

RUTH C. MASON
Attesting Officer

DONALD W. BANNER
Commissioner of Patents and Trademarks